US010967037B2

(12) United States Patent
Gee

(10) Patent No.: US 10,967,037 B2
(45) Date of Patent: Apr. 6, 2021

(54) PROCESS OF PREPARING VITAMIN E CONCENTRATE

(71) Applicant: Palm Nutraceuticals Sdn. Bhd., Selangor (MY)

(72) Inventor: Ping Tou Gee, Petaling Jaya (MY)

(73) Assignee: PALM NUTRACEUTICALS SDN. BHD., Petaling Jaya (MY)

( * ) Notice: Subject to any disclaimer, the term of this patent is extended or adjusted under 35 U.S.C. 154(b) by 193 days.

(21) Appl. No.: 16/115,118

(22) Filed: Aug. 28, 2018

(65) Prior Publication Data

US 2019/0282649 A1    Sep. 19, 2019

(30) Foreign Application Priority Data

Mar. 16, 2018  (MY) .......................... PI 2018701060

(51) Int. Cl.
*A61K 36/889* (2006.01)
*A23L 33/105* (2016.01)
*A61K 31/355* (2006.01)

(52) U.S. Cl.
CPC .......... *A61K 36/889* (2013.01); *A23L 33/105* (2016.08); *A61K 31/355* (2013.01); *A23V 2002/00* (2013.01)

(58) Field of Classification Search
None
See application file for complete search history.

(56) References Cited

U.S. PATENT DOCUMENTS 7,507,847 B2 *   3/2009   Tou .......................... C11B 3/001
                                                              454/67
9,512,098 B1 *   12/2016  Howard ................ C07D 311/72

FOREIGN PATENT DOCUMENTS

EP          1693435 A1 *   8/2006  ................ C11B 7/00
WO   WO-2013068443 A1 *   5/2013  ................ C11B 3/10
WO   WO-2015121156 A1 *   8/2015  ................ C11B 3/008

OTHER PUBLICATIONS

Gee, Ping Tou, Unleashing the untold and misunderstood observations on vitamin E, Genes Nutr, 6:5-16, Jul. 20, 2010, 12 pages.
Gee, Ping Tou et al., Vitamin E analysis by ultra-performance convergence chromatography and structural elucidation of novel x-tocodienol by high-resolution mass spectrometry, Food Chemistry, 196:367-373 (2016), 7 pages.
NutraSource, Generally Recognized as Safe (GRAS) Determination for the Use of Palm Tocotrienol Rich Fractions (TRF) as Ingredients in Food, Oct. 2009, 180 pages.
Heinonen et al., The Tocopheral, Tocotrienol, and Vitamin E Content of the Average Finnish Diet, Internat. J. Vit. Nutr. Res. 61:27-32 (1991), 6 pages.
Ikeda, Saiko et al., Dietary x-Tocopherol Decreases x-Tocotrienol by not y-Tocotrienol Concentration in Rats, J. Nutr., 133: 428-434 (2003), 7 pages.
Khanna, Savita et al., Delivery of orally supplemented x-tocotrienol to vital organs of rats and tocopheraol-transport protein deficient mice, Free Radical Biology & Medicine, 39:1310-1319 (2005), 10 pages.
Khanna, Savita et al., Excessive x-tocopherol exacerbates microglial activation and brain injury caused by acute ischemic stroke, FASEB J., 29, article fj.14-263723 (2015), 9 pages.
Kushi, Lawrence et al., Dietary Antioxidant Vitamins and Death from Coronary Heart Disease on Postmenopausal Women, The New England Journal of Medicine, 334:1156-1162 (1996), 7 pages.
Morris, Martha Clare et al., Dietary Intake of Antioxidant Nutrients and the Risk of Incident Alzheimer Disease in a Biracial Community Study, JAMA, 287(24): 3230-3237 (2002), 8 pages.
Patel, Viren et al., Oral Tocotrienols are Transported to Human Tissues and Delay the Progression of the Model for End-Stage Liver Disease Score in Patients, The Journal of Nutrition, 142:513-519, Feb. 1, 2012, 7 pages.
Peralta, Elizabeth et al., Effect of vitamin E on tamoxifen-treated breast cancer cells, Surgery, 140:607-615 (2006), 9 pages.
Peralta, Elizabeth et al., Vitamin E Increases Biomarkers of Estrogen Stimulation when Taken with Tamoxifen, Journal of Surgical Research, 153:143-147 (2009), Jan. 7, 2008, 5 pages.
Shibata, Akira et al., x-Tocopherol attenuates the cytotoxic effect of y-tocotrienol in human colorectal adenocarcinoma cells, Biochemical and Biophysical Research Communications 397:214-219 (2010), 6 pages.
Shibata, Akira et al., x-Tocopherol suppresses antiangiogenic effect of y-tocotrienol in human umbilical vein endothelial cells, ScienceDirect, Journal of Nutritional Biochemistry 26:345-350 (2015), 6 pages.
Sookwong, Phumon et al., Tocotrienol Distribution in Foods: Estimation of Daily Tocotrienol Intake of Japanese Population, Journal of Agricultural and Food Chemistry Article, 58:3350-3355 (2010), 6 pages.
Uchida, Tomono et al., Tissue Distribution of x- and y-Tocotrienol and y-Tocopherol in Rats and Interference with Their Accumulation by x-Tocopherol, AOCS, Lipids, 47:129-139 (2012), 11 pages.

(Continued)

*Primary Examiner* — Russell G Fiebig
(74) *Attorney, Agent, or Firm* — Loza & Loza, LLP; Michael F. Fedrick

(57) ABSTRACT

The present invention discloses a process for modifying the natural composition of tocotrienol-rich fraction to achieve a product with reduced α-tocopherol content, enhanced β- and δ-tocotrienol content and also with an enriched total tocotrienol concentration.

25 Claims, 1 Drawing Sheet

(56) References Cited

OTHER PUBLICATIONS

Uchihara, Yuki et al., Alpha-tocopherol attenuates the anti-tumor activity of crizotinib against cells transformed by NPM-ALK, PLOS ONE, 12(8): e0183003 (2017), 22 pages.

Wu, Qi-Jun et al., Vitamin E intake and the lung cancer risk among female nonsmokers: a report from the Shanghai Women's Health Study, National Institute of Health Public Access 136(3): 610-617, Feb. 15, 2015, 17 pages.

\* cited by examiner

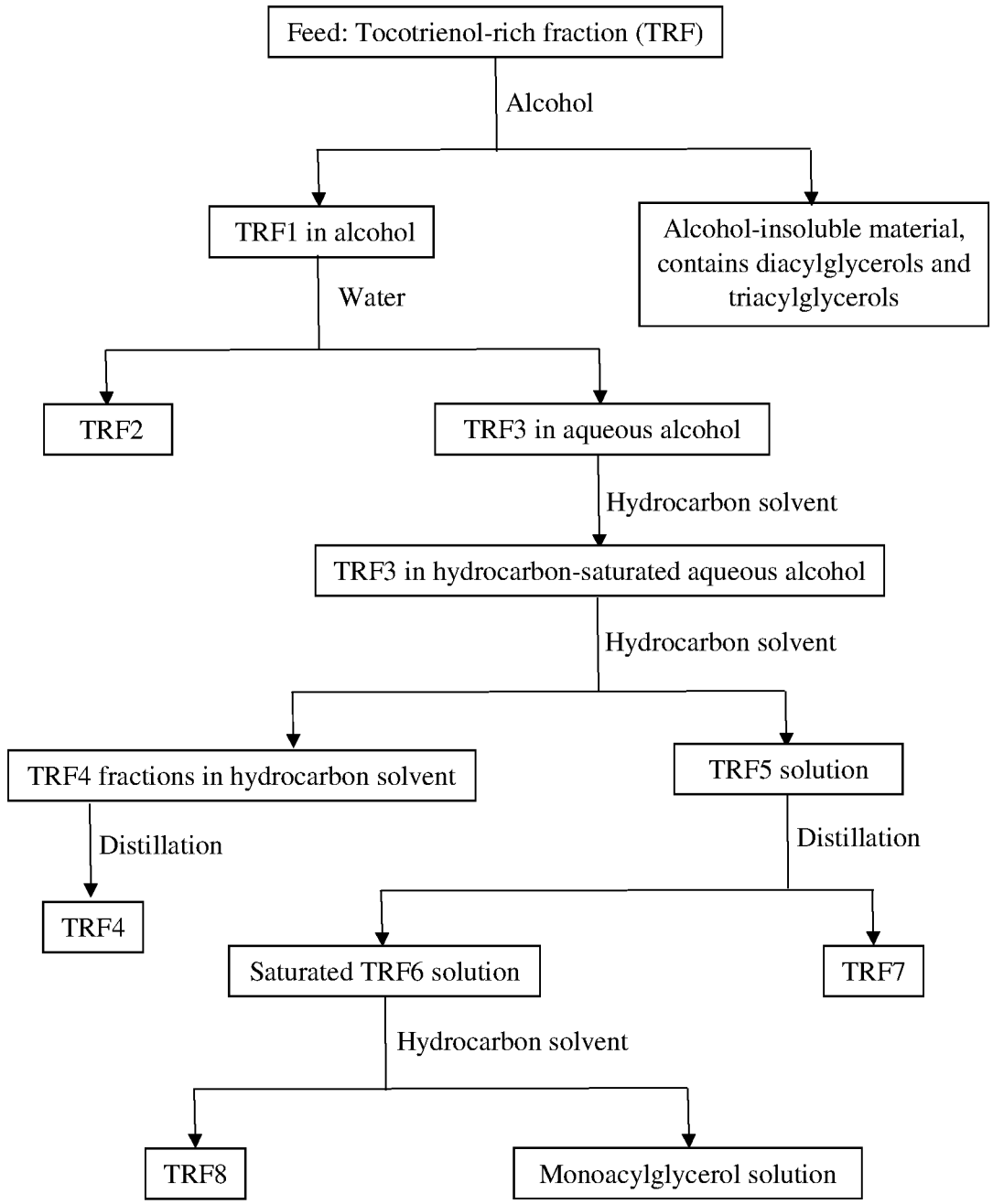

PROCESS OF PREPARING VITAMIN E CONCENTRATE

TECHNICAL FIELD OF THE INVENTION

This invention relates to a process for modifying the composition of tocotrienol-rich fraction or vitamin E concentrate. More specifically, the invention is concerned with removal of α-tocopherol from Vitamin E concentrate or enhancing β- and δ-tocotrienol content in the vitamin E concentrate, or both, and produces new products of tocotrienol-rich fraction with reduced α-tocopherol content, enhanced β- and δ-tocotrienol content, or both, by way of solvent extractions and fractionations.

BACKGROUND OF THE INVENTION

International Union of Pure and Applied Chemistry and International Union of Biochemistry Joint Commission on Biochemical Nomenclature recommended that "the term vitamin E should be used as a general descriptor for all tocol and tocotrienol derivatives that exhibit qualitatively the biological activity of α-tocopherol". Therefore the term "vitamin E" was referred to four forms of tocopherol and four forms of tocotrienol. Subsequently, discovery of tocomonoenols and α-tocodienol were reported. These compounds can also be included as vitamin E There are 16 forms of natural vitamin E, however, β-, γ- and δ-tocodienols have yet to be discovered (Gee et al., 2016, Food Chem., 196: 367-373). Tocomonoenols and α-tocodienol are minor or trace vitamin E components.

Unlike tocopherols, natural sources of tocotrienols are less common. The Japanese national dietary consumption of tocopherols and tocotrienols are 8.82-10.7 and 1.86-2.15 mg/day/person, respectively (Sookwong et al., 2010, J. Agric. Food Chem. 58, 3350-3355) whereas that for the Finnish are 18.59 and 4.21 mg/day/person, respectively (Heinonen & Piironen, 1991, Int. J. Vitam. Nutr. 61, 27-32). National dietary consumption data of tocotrienols for other countries are unavailable. The current recommended vitamin E dietary allowance in the United States dietary reference intake is 15 mg/day of 2R-stereoisomers of α-tocopherol, all other forms of vitamin E are excluded.

Commercial sources of tocotrienols are palm oil, rice bran oil and annatto beans. Tocotrienols extracted from these natural sources have different vitamin E composition. Crude palm oil is the most reliable natural source of Vitamin E, in particular tocotrienols because of its annual production volume (availability). Typically, crude palm oil contains 600-1,000 mg/kg of vitamin E.

Crude palm oil can undergo transesterification with methanol, produces fatty acid methyl esters (commonly used as biodiesel) and glycerol. Tocotrienols are concentrated from the fatty acid methyl esters fraction by vacuum distillation and post-distillation treatment such as using absorbents. These are described in U.S. Pat. Nos. 5,157,132, 6,072,092, and 5,190,618, European Patent No. 0333472A2, U.K. Patent No. GB2218989A, GB2160874A and GB1515238. Vitamin E can also be extracted from crude palm oil by alcohol prior to vacuum distillation as described in U.S. Pat. No. 6,649,781 and U.K. Patent No. GB2387390. U.S. Pat. No. 7,507,847 teaches a process to extract vitamin E from crude palm oil using liquid-liquid extraction and urea-inclusion complex to remove the non-vitamin E components.

Vitamin E can also be recovered from fatty acid distillates after esterification and vacuum distillation (U.S. Pat. Nos. 5,190,618, 6,224,717) or after hydrolysis and vacuum distillation (U.S. Pat. No. 8,673,967).

The enriched tocotrienol product is commonly called tocotrienol-rich fraction or tocotrienol concentrate. It is a mixture of vitamin E and other natural components. For palm oil, the vitamin E mixture comprises α-tocopherol, α-tocomonoenol, α-tocotrienol, β-tocotrienol, γ-tocotrienol, δ-tocotrienol and traces of α-tocodienol (Gee et al., 2016, Food Chem., 196, 367-373). Data extracted from the original submission of Generally Recognised As Safe (GRAS) determination for the use of palm tocotrienol rich fraction dated 19 Oct. 2009 indicated that the range of α-tocopherol content of tocotrienol-rich fraction is from 20.0% to 27.6%, whereas that of δ-tocotrienol is from 10.3% to 15.6% (GRAS Notice No. 307). Tocotrienol-rich fraction also contains squalene, sterols, monoacylglycerols, diacylglycerols and triacylglycerols.

Natural composition of tocotrienol-rich fraction derived from palm oil and rice bran oil is not ideal for long-term consumption. This is because α-tocopherol is known to inhibit the absorption of other forms of vitamin E (Ikeda et al., 2003, J. Nutr. 133, 428-434; Khanna et al., 2005, Free Radic. Biol. Med. 39, 1310-1319; Gee 2011, Genes Nutr. 6, 5-16; Uchida et al. 2012, Lipids 47, 129-139). Raw data in a study on healthy humans (Patel et al., 2012, J. Nutr. 142, 513-519) shows that the tocotrienol concentrations in the whole blood sample after supplementation with tocotrienol-rich fraction for 12 weeks is lower than that after supplementation for 6 weeks for all the men and more than half of the women. These data further demonstrated that α-tocopherol suppresses the absorption of tocotrienols in humans after 6 weeks of supplementation with the tocotrienol-rich fraction under the trial conditions.

α-Tocopherol attenuates anti-cancer activities of tocotrienols (Shibata et al., 2010, Biochem. Biophys. Res. Comm. 397, 214-219 and Shibata et al., 2015, J. Nutr. Biochem. 26, 345-350) and exacerbates stroke injury (Khanna et al., 2015, FASEB J. 29, 828-836). α-Tocopherol is an antagonist to tamoxifen (Peralta et al., 2006, Surgery 140, 607-615; Peralta et al., 2009, J. Surg. Res. 153, 143-147) and crizotinib (Uchihara et al., 2017, PLoS One 12, e0183003) in cancer treatments. In addition, meta-analysis demonstrates that α-tocopherol supplementation increases all-cause mortality (Gee 2011, Genes Nutr. 6, 5-16).

It is important to highlight that α-tocopherol is not harmful at nutritional concentrations but α-tocopherol supplementation has detrimental health effects. Dietary intake of α-tocopherol non-significantly reduces the lung cancer incidence whereas α-tocopherol supplementation significantly increases the lung cancer incidence in the Shanghai Women's Health Study (Wu et al. 2015, Int. J. Cancer 136, 610-617). Dietary α-tocopherol, but not α-tocopherol supplement decreases the incidence of death from coronary heart disease in postmenopausal women (Kushi et al. 1996, New Engl. J. Med. 334, 1156-1162) and the incidence of Alzheimer disease in an aged population (Morris et al. 2002 JAMA 287, 3230-3237).

From bioavailability, nutritional and chemoprevention potency viewpoints, it is desirable to reduce the α-tocopherol content in tocotrienol-rich fraction. However, it may not be necessary to eliminate the α-tocopherol because it is present in food (since dietary intake of α-tocopherol is unavoidable) and also at low concentration such as that available from dietary intake, α-tocopherol is not harmful. Therefore, it may not be worthwhile to remove the α-tocopherol totally. It is also desirable to increase the δ-tocotrienol content in the tocotrienol-rich fraction because it has the highest potency in anti-cancer activities (Shibata et al., 2010, *Biochem. Biophys. Res. Comm.* 397, 214-219).

There are already patents on modification of tocotrienol-rich fraction composition. U.S. Pat. Nos. 6,395,915, 6,656,358 and 2004/0026323 describe chromatographic separation of vitamin E components. U.S. Pat. No. 8,937,191 teaches a process to produce high purity α-tocotrienol and other vitamin E enriched fractions from palm oil extract using a combination of solid phase extraction and simulated moving bed separation technology. U.S. Pat. No. 9,512,098 teaches a process to produce purified γ- and δ-tocotrienols from palm oil or rice bran oil tocotrienol-rich fraction using flash chromatography with a binary mobile phase gradient elution. U.S. Pat. No. 8,575,369 involves a process to produce α-tocotrienol with purity greater than 80% by alkylation of non-α-tocotrienol in tocotrienol-rich fraction at carbons-5 and 7, separation of the alkylated tocotrienols from α-tocotrienol and subsequently reduction of alkylated tocotrienols to form α-tocotrienol and combined with the non-alkylated α-tocotrienol.

U.S. Pat. No. 6,224,717 teaches a step to fractionate tocotrienol-rich fraction obtained from fatty acid distillates using polar organic solvents (excludes neat alcohols) that are miscible with water including using neat alcohol and heptane as extracting solvents, and using aqueous alcohol as solvent. However, the inadequately described process does not provide much information. In the case of a process involving extraction at 45° C. for 3 hours and separation by centrifugation at 1512 times the gravitational force for 10 minutes, both the extract and raffinate have undetectable α-tocopherol content, with an undisclosed feed material but the α-tocopherol content of such feed material is expected to be high. The composition of extract and raffinate indicates that the process is inefficient as compare to the present invention. Other than undetectable α-tocopherol content in both extract and raffinate (which is illogical), the ratio of vitamin E components in the extract to that in the raffinate range from 2.14 (δ-tocopherol) to 4.93 (α-tocotrienol) as reflected by Example 8 of U.S. Pat. No. 6,224,717. Such ratios are inadequate for our object. In the case of fractionation using aqueous methanol (Examples 15 and 16 of U.S. Pat. No. 6,224,717), the results as shown in Tables 5 and 6 of U.S. Pat. No. 6,224,717 similarly indicate that the process is inefficient as compare to the present invention. Table 5 of U.S. Pat. No. 6,224,717 indicates that α-tocopherol, β-tocopherol, γ-tocopherol, δ-tocopherol, α-tocotrienol, γ-tocotrienol and δ-tocotrienol contents of feed and extract expressed as % of total vitamin E for extraction using 93% aqueous methanol are 38.1, 21.0, 1.4, 1.4, 11.3, 25.5, 1.2% and 29.1, 21.9, 1.5, 1.9, 10.2, 33.6, 1.8%, respectively. The total vitamin E concentration of the feed and extract is 14.57 and 40.57%, respectively. The composition of the feed and extract indicate that the removal of α-tocopherol is inadequate whereas the enhancement of tocotrienols is also inadequate. The corresponding composition of the raffinate is 65.2, 21.7, 2.4, 1.4, 0.0, 9.1, 0.4%, respectively. The raffinate has very low total vitamin E concentration (5.08%). Both the extract and raffinate are not good enough to be used for clinical applications.

Table 5 of U.S. Pat. No. 6,224,717 also indicates that α-tocopherol, β-tocopherol, γ-tocopherol, δ-tocopherol, α-tocotrienol, γ-tocotrienol and δ-tocotrienol contents of feed and extract expressed as % of total vitamin E for extraction using 85% aqueous methanol are 38.1, 21.2, 1.9, 1.5, 9.8, 26.1, 1.4% and 19.5, 17.8, 1.5, 2.3, 13.1, 42.8, 3.0%, respectively. The total vitamin E concentration of the feed and extract is 13.00 and 30.24%, respectively. The composition of the feed and extract indicate that the removal of α-tocopherol has improved over that that extracted with 93% aqueous methanol whereas the enhancement of tocotrienols has improved. The corresponding composition of the raffinate is 46.8, 23.7, 1.9, 1.3, 8.4, 17.9, 0.0%, respectively. The raffinate has very low total vitamin E concentration (9.91%). Both the extract and raffinate are still not good enough to be used for clinical applications.

In view of the fact that the removal of α-tocopherol from the feed material is inadequate and whereas the enhancement of tocotrienols in the raffinate is also inadequate as described in U.S. Pat. No. 6,224,717, the present invention has provided a novel process for the removal of α-tocopherol from Vitamin E concentrate or enhancing the δ-tocotrienol content in Vitamin E concentrate. The process of the present invention will enable one to produce new products of tocotrienol-rich fraction with reduced α-tocopherol content and with enhanced δ-tocotrienol content, or both, by way of solvent extractions and fractionations. The new products produced according to the process of the present invention, namely, the tocotrienol-rich fraction with reduced α-tocopherol content and with enhanced δ-tocotrienol content are suitable for use in clinical applications.

The process of producing tocotrienol-rich fraction with reduced α-tocopherol content and with enhanced δ-tocotrienol content, or both, by way of solvent extractions and fractionations of the present invention consists of several novel features and a combination of features hereinafter will now be fully described and illustrated in the accompanying description and FIGURE. It is being understood that various changes in the details may be made to the invention without departing from the scope of the invention or sacrificing any of the advantages of the present invention.

SUMMARY OF THE INVENTION

The primary object of the present invention is to provide a process for the removal of α-tocopherol in tocotrienol-rich fraction (TRF) and to provide a tocotrienol-rich fraction with low α-tocopherol content for clinical applications. Another object of the present invention is to provide a process for enhancing the β- and δ-tocotrienols in the tocotrienol-rich fraction and to provide a tocotrienol-rich fraction with enhanced β- and δ-tocotrienols contents for clinical applications. Yet another object of the present invention is to provide a process for the removal of non-tocotrienol components from the tocotrienol-rich fractions, thereby enriching the tocotrienol contents in the tocotrienol-rich fraction.

These objects of the present invention are accomplished by providing a process to fractionate tocotrienol-rich fraction into several useful products as demonstrated in the present invention. The preferred embodiment of the present invention first removes alcohol-insoluble materials from tocotrienol-rich fraction with neat methanol. Water is then added to obtain a saturated aqueous methanolic solution of tocotrienol-rich fraction after removal of the alcohol-insoluble materials. This saturated tocotrienol-rich fraction in aqueous methanolic solution is then saturated with n-hexane and separated from the bottom oily layer. The saturated mixture is further extract with multiple aliquots of n-hexane. The extracts are then subjected to distillation. The raffinate is subjected to distillation, phase separation and/or further extraction of tocotrienol-rich fraction with n-hexane.

Accordingly, the first aspect of the present invention is that there is provided a process for modifying the composition of Vitamin E in tocotrienol-rich fraction (TRF) characterized by reducing or removing α-tocopherol content from TRF feed material and/or enhancing the content of β- and δ-tocotrienol in Vitamin E concentrate by the process of solvent extraction and fractionation of TRF feed material.

The second aspect of the present invention is that there is provided a process of solvent extraction and fractionation for reducing or removing α-tocopherol and enhancing the content of β- and δ-tocotrienol in vitamin E concentrate characterized by subjecting the TRF feed material to a process comprising the steps of:
a. Dissolving the tocotrienol-rich fraction (TRF) feed material in an alcohol;
b. Removing the alcohol-insoluble components from the tocotrienol-rich fraction 1 (TRF1) solution;
c. Adding water to TRF1 solution to separate tocotrienol-rich fraction 2 (TRF2) from the saturated tocotrienol-rich fraction 3 (TRF3) solution;
d. Saturating the TRF3 solution in aqueous alcohol with a hydrocarbon solvent;
e. Extracting from the hydrocarbon-saturated aqueous alcohol TRF3 solution with addition of additional aliquot of hydrocarbon solvent to obtain tocotrienol-rich fraction 4 (TRF4) in hydrocarbon solvent and tocotrienol-rich fraction 5 (TRF5);
f. Separating TRF4 solution from TRF5 solution obtained in step (e);
g. Obtaining TRF4 by way of distillation of TRF4 solution obtained in step (f);
h. Partial removal of the aqueous alcohol from TRF5 solution obtained in step (f) above by further distillation to obtain saturated tocotrienol-rich fraction 6 (TRF6) solution and tocotrienol-rich fraction 7 (TRF7);
i. Adding hydrocarbon solvent to the saturated TRF6 solution obtained in step (h) above to obtain tocotrienol-rich fraction 8 (TRF5) and highly polar monoacylglycerol raffinate; and
j. Removal of solvent residue in TRF7 and TRF8 by distillation.

The third aspect of the present invention is that the tocotrienol-rich fraction (TRF) feed material used is derived from palm oil or palm fatty acid distillates or rice bran oil.

In the fourth aspect of the present invention, the tocotrienol-rich fraction containing α-tocopherol is derived from materials other than palm oil or palm fatty acid distillates or rice bran oil, such as for example, oils or extracts from barley, oat, rye, wheat, palm fruits, palm pressed mesocarp fiber, other palm oil fractions such as palm olein and palm stearin, and these are used as feed material.

The fifth aspect of the present invention is that the alcohol used in the process is methanol or ethanol or a mixture of methanol and ethanol or aqueous 1-propanol or 2-propanol and that the amount of water added has an alcohol to water ratio preferably of 10:1 v/v and more preferably 15:1 v/v.

The sixth aspect of the present invention is that the hydrocarbon solvent used in the process is n-hexane, hexanes or n-heptane or a mixture of two or more of these hydrocarbon solvents and that the hydrocarbon-saturated tocotrienol-rich fraction 3 (TRF3) is extracted with multiple aliquots of hydrocarbon solvent.

The seventh aspect of the present invention is that the tocotrienol-rich fraction 2 (TRF2) and tocotrienol-rich fraction 4 (TRF4) or a portion thereof with an enriched total tocotrienol content and/or with a wide range of tocotrienol product composition can be recycled and used as a feed material in the process.

The eighth aspect of the present invention is that the process produces TRF7 and/or TRF8 which provides a wide range of tocotrienol products with an enriched total tocotrienol content, with reduced α-tocopherol content and/or enhanced δ- and β-tocotrienols content. The tocotrienol products produced according to the process of the present invention have an α-tocopherol content preferably less than 7% of the total vitamin E content by weight, more preferably less than 5% of the total vitamin E content by weight and even more preferably less than 1% of the total vitamin E content by weight and most preferably less than 0.5% of the total vitamin E content by weight. Furthermore, the tocotrienol products produced according to the process of the present invention have a δ-tocotrienol content preferably exceeding 29% of the total vitamin E content by weight, more preferably exceeding 35% of the total vitamin E content by weight and most preferably exceeding 45% of the total vitamin E content by weight. Accordingly, the tocotrienol products with an enriched total tocotrienol content, with reduced α-tocopherol content and/or enhanced β- and δ-tocotrienols content can be used in clinical applications.

The ninth aspect of the present invention provides for a process for the removal of monoacylglycerols, triacylglycerols and diacylglycerols from the tocotrienol-rich fraction (TRF) using aqueous alcohol and the removal of the monoacylglycerols can be carried out with or without the removal of alcohol-insoluble materials. Furthermore the removal of monoacylglycerols, triacylglycerols and diacylglycerols from the TRF can involve a two-step methanol extraction process.

According to the tenth aspect of the present invention, water can be used in the process to enhance the fractionation of α-tocopherol preferentially into the n-hexane phase and the β-aid δ-tocotrienols into the methanol phase. The fractionation process can be carried out at room temperature and under normal atmospheric pressure (101,325 Pa).

According to the eleventh aspect of the present invention, the process also produces TRF7 and TRF8 fractions or their combined fractions and these products have low α-tocopherol content, high β- and δ-tocotrienol content and high total tocotrienol content and can be used in clinical applications.

According to the twelfth aspect of the present invention, the distillation of aqueous methanol and n-hexane using the process of the present invention is carried out by using a rotary evaporator or a falling film evaporator, a thin film evaporator or using any suitable distillation vessels under reduced pressure (lower than atmospheric pressure), preferably between 30,000-90,000 Pa. Furthermore, the TRF5 solution is distilled under partial vacuum until the clear solution turns milky to form the TRF6 solution emulsion as the top layer and with TRF7 as the bottom layer.

The process for the removal of α-tocopherol in tocotrienol-rich fraction (TRF) to provide a tocotrienol-rich fraction with low α-tocopherol content and with enhanced β- and δ-tocotrienols in the tocotrienol-rich fraction for clinical applications of the present invention consists of several novel features and a combination thereof will hereinafter fully described and illustrated in the accompanying description and FIGURE, it being understood that various changes in the details may be made without departing from the scope of the invention or sacrificing any of the advantages of the present invention and which is defined by the appended claims.

BRIEF DESCRIPTION OF THE FIGURE

The present invention will be fully understood from the detailed description given herein below and the accompanying FIGURE which is given by way of illustration only, and thus are not limitative of the present invention, wherein:

FIG. 1 shows a flow diagram of the process of the present invention.

DETAILED DESCRIPTION OF THE INVENTION

The features and details of the invention, either as steps of the invention or as combinations of parts of the invention will now be described. It will be understood that the embodiments of the invention are shown by way of illustration and not as limitations of the invention. The principle features of the invention may be employed in various embodiments without departing from the scope of the invention.

The present invention is accomplished by providing a process to fractionate tocotrienol-rich fraction into several useful products. Tocotrienol-rich fraction (TRF) is a material derived from plants which contains tocotrienol. Tocotrienol is preferably present in such materials in amounts of greater than 10% (w/w), more preferably greater than 30% (w/w), more preferably greater than 50% (w/w), more preferably greater than 60% (w/w), and even more preferably greater than 70% (w/w). TRF can be obtained from seeds, nuts and grains such as rice, wheat, barley, rye, oats, hazelnuts, or maize, and preferably from oils or other processed derivatives of such materials, such as palm oil, palm fatty acid distillates, rice bran oil, olive oil, or wheat germ, or can be obtained from other plant materials such as saw palmetto or anatto.

According to the present invention, the process first removes alcohol-insoluble materials from tocotrienol-rich fraction with neat methanol. Water is then added to obtain a saturated aqueous methanolic solution of tocotrienol-rich fraction after removal of the alcohol-insoluble materials. This saturated tocotrienol-rich fraction in aqueous methanolic solution is then saturated with n-hexane and separated from the bottom oily layer. The saturated mixture is further extract with multiple aliquots of n-hexane. The extracts are then subjected to distillation. The raffinate is further subjected to distillation, phase separation and/or further extraction of tocotrienol-rich fraction with n-hexane.

The present invention uses commercial tocotrienol-rich fraction as the feed material and the process can be carried out at room temperature and under atmospheric pressure (101,325 Pa). The process does not involve chromatography or addition of absorbent. Commercial tocotrienol-rich fraction feed material includes palm fatty acid distillates, such as that listed in the tables of GRAS Notice No. 307 dossier (i.e. Tocomin® 30%, Tocomin® 50%, DVL30, DVL50, DVL70, Carotino TRF 10%, Carotino TRF 20%, Carotino TRF 50%, Carotino TRF 80%, Gold Tri E30, Gold Tri E50, Gold Tri E70, Super T25, Super T30, Super T50 and Super T80), Vitrenol 30L, Vitrenol 40L, Vitrenol SOL, Vitrenol 70L and Fortrienol™ containing 10%, 30% and 50% concentration by weight of TRF.

The less polar components of tocotrienol-rich fraction such as triacylglycerols and diacylglycerols can be separated from the more polar components such as vitamin E and monoacylglycerols by dissolving the more polar components in neat methanol. The step can be repeated i.e. re-extracting the raffinate with fresh neat methanol, until all or almost all the tocotrienols have been extracted. The methanolic extracts are pooled to form the tocotrienol-rich fraction 1 (TRF1) solution. It is understood that the methanolic extracts can also be processed individually.

In general, methanol and n-hexane are immiscible solvents. However, the mixture containing n-hexane, methanol and tocotrienol-rich fraction (feed) forms a single phase at room temperature under atmospheric pressure.

Water is added to TRF1 solution. The solubility of tocotrienol-rich fraction in the aqueous methanolic phase decreases, causing a phase separation where the excess tocotrienol-rich fraction 2 (TRF2) forms the bottom oily layer, separate from the saturated aqueous methanolic solution of tocotrienol-rich fraction 3 (TRF3). TRF2 has higher α-tocopherol content and lower δ-tocotrienol contents than TRF3. TRF2 and TRF3 are separated. The amount of water added affects the yield and vitamin E composition in TRF2 and TRF3. TRF2 can be recycled as a feed material.

The functions of adding water to the methanolic extract are to produce a saturated solution of tocotrienol-rich fraction in aqueous methanol, to facilitate phase separation for methanol and n-hexane in the presence of tocotrienol-rich fraction, and also to enhance fractionation of α-tocopherol preferentially into the n-hexane phase and, β-, and δ-tocotrienols into the methanol phase. Two separate steps of methanol extraction and addition of water is preferred over a single step of extraction with aqueous methanol because the former can remove significant amount of triacylglycerols, diacylglycerols and small amount of α-tocopherol prior to further processing. These components have impacts on the subsequent process and also on product characteristics. In the process of the present invention, the amount of water added has an alcohol to water ratio preferably of 10:1 v/v and more preferably 15:1 v/v.

Saturated aqueous alcoholic TRF3 solution is then saturated with n-hexane. When the amount of n-hexane added is less than that required to saturate the aqueous methanolic solution, no phase separation can be obtained. Further addition of small volumes of n-hexane to the saturated solution preferentially fractionates α-tocopherol into the n-hexane layer and δ-tocotrienol in the aqueous methanol layer. This step can be repeated until most of the α-tocopherol has been gradually fractionated into the tocotrienol-rich fraction 4 (TRF4) in n-hexane. After solvent removal by distillation, TRF4 fractions are obtained. It is important to use multiple aliquots but small volume in each aliquot for better selectivity in fractionation of α-tocopherol into the hydrocarbon layer. In general, TRF 4 fractions have decreasing α-tocopherol content, increasing β- and δ-tocotrienols content, and increasing total tocotrienol content as compare with the preceding fraction. TRF4 fractions can be recycled as a feed material.

The raffinate after n-hexane extractions is the tocotrienol-rich fraction 5 (TRF5) solution. TRF5 solution is distilled under partial vacuum until the clear solution turns milky and forms the tocotrienol-rich fraction 6 (TRF6) solution/emulsion with tocotrienol-rich fraction 7 (TRF7) separates as the bottom layer. n-Hexane can be used to extract additional tocotrienol-rich fraction 8 (TRF8) from the solution/emulsion, leaving the monoacylgyceols containing raffinate. TRF7 has a total tocotrienol content exceeding 50% by weight whereas TRF8 generally have a tocotrienol content exceeding 50% except when excessive monoacylglycerols are also extracted into the hydrocarbon layer. It is understood that methanol can be completely distilled off from TRF5 if a tocotrienol-rich fraction containing monoacylglycerols is preferred. It is also understood that it may not necessary to separate TRF7 from the mixture. Both TRF7 and TRF8 can be combined in the n-hexane layer prior to separation. TRF7 and TRF8 or their combined fractions are the main tocotrienol product that are having low α-tocopherol content, high β-, and δ-tocotrienols content and also high total tocotrienol content. The enhancement of γ-tocotrienol in the tocotrienol product is less significant as compare with β- and δ-tocotrienols. There is a reduction in α-tocotrienol but to a lesser extent as compare with α-tocopherol.

Distillation of solvents (aqueous methanol and n-hexane) can be carried out by using rotary evaporator, falling film evaporator, thin film evaporator or any suitable distillation vessels under reduced pressure, preferably between 30,000-90,000 Pa.

Although less efficient, the objects can also be achieved by removing monoacylglycerols with aqueous methanol immediately after or without removal of methanol-insoluble materials.

DESCRIPTION OF PREFERRED EMBODIMENTS

The present invention will now be further specifically described by the following examples. Vitamin E composition is analysed by normal-phase high-performance liquid chromatography-fluorescence detector and non-vitamin E components are analysed by gas liquid chromatography-flame ionisation detector.

Example I 973.29 g of TRF was extracted with 2.0 L neat methanol in a separating funnel. The bottom oily layer was separated and re-extracted with another 2.0 L neat methanol. The step was repeated and the material was extracted for a total of 10 times. The methanol-insoluble material (residue) was rotary evaporated and 104.80 g was obtained. Gas liquid chromatogram reflects that the residue contains mainly triacylglycerols and diacylglycerols. 2.0 L of distilled water was added to the pooled methanol extract TRF1 (20 L). An oily layer was separated as the bottom layer and rotary evaporated to obtain 383.06 g TRF2. 1.2 L of n-hexane was added to saturate the saturated aqueous methanolic TRF3 solution and the solution was extracted with additional 2.0 L n-hexane. The upper layer is TRF4 in n-hexane and the solution was rotary evaporated to dryness to remove n-hexane. 119.07 g of TRF4 was obtained. The bottom TRF5 layer is rotary evaporated until the clear solution turn milky. A bottom oily layer separates from the top TRF6 solution. After rotary evaporation of the oily layer, 128.65 g of TRF7 was obtained. TRF6 solution was extracted five times with 100 mL n-hexane each. The TRF8 solutions are pooled and rotary evaporated to obtain 11.91 g of TRF8. The raffinate is a solution containing monoacylglycerols. Table 1 summarises the characteristics of the fractions obtained.

TABLE 1

Characteristics of the fractions in Example I

| | Weight (g) | $T_3$ (%)$^S$ | VE (%)$^S$ | α-T (%)$^E$ | α-$T_1$ (%)$^E$ | α-$T_3$ (%)$^E$ | β-$T_3$ (%)$^E$ | γ-$T_3$ (%)$^E$ | δ-$T_3$ (%)$^E$ |
|---|---|---|---|---|---|---|---|---|---|
| Feed | 973.29 | 23.5 | 33.4 | 27.3 | 2.4 | 26.7 | 2.4 | 32.0 | 9.3 |
| Residue | 81.86 | 0.4 | 1.3 | 65.3 | 3.4 | 20.3 | nd | 11.0 | nd |
| TRF2 | 383.06 | 25.0 | 37.0 | 29.6 | 2.8 | 27.3 | 1.1 | 34.0 | 5.3 |
| TRF4 | 119.07 | 44.3 | 59.8 | 21.9 | 4.1 | 27.0 | 2.2 | 35.8 | 9.0 |
| TRF7 | 128.65 | 61.4 | 68.1 | 8.7 | 1.2 | 23.1 | 3.1 | 45.2 | 18.7 |
| TRF8 | 11.91 | 57.9 | 58.8 | 1.4 | 0.1 | 16.6 | 4.0 | 41.5 | 31.4 |

Abbreviations:
VE—vitamin E;
T—tocopherol;
$T_1$—tocomonoenol;
$T_3$—tocotrienol;
(%)$^S$—% on sample;
(%)$^E$—% of total vitamin E content;
nd—not detected (below detection limit).

Example II 997.35 g of TRF was extracted with 2.0 L neat methanol in a separating funnel. The bottom oily layer was separated and re-extracted with another 2.0 L neat methanol. The step was repeated and the material was extracted for a total of 10 times. The methanol-insoluble material (residue) was rotary evaporated and 107.39 g was obtained (the content contains mainly triacylglycerols and diacylglycerols). 2.0 L of distilled water was added to the pooled methanol extract TRF1 (20 L). An oily layer was separated as the bottom layer and rotary evaporated to obtain 366.95 g TRF2. The TRF3 extract was saturated with 1.2 L n-hexane and extracted with 10 aliquots of 200 mL n-hexane each. The upper layer is TRF4 in n-hexane and the solution was rotary evaporated to dryness to remove n-hexane. The bottom TRF5 layer is rotary evaporated until the clear solution turn milky. A bottom oily layer separates from the top TRF6 solution. After rotary evaporation of the oily layer, 76.78 g of TRF7 was obtained. TRF6 solution was extracted five times with 100 mL n-hexane each. The TRF8 solutions are pooled and rotary evaporated to obtain 11.42 g of TRF8. The raffinate is a solution containing monoacylglycerols. Table 2 summarises the characteristics of the fractions obtained.

TABLE 2

Characteristics of the fractions in Example II

| | Weight (g) | $T_3$ (%)$^S$ | VE (%)$^S$ | α-T (%)$^E$ | α-$T_1$ (%)$^E$ | α-$T_3$ (%)$^E$ | β-$T_3$ (%)$^E$ | γ-$T_3$ (%)$^E$ | δ-$T_3$ (%)$^E$ |
|---|---|---|---|---|---|---|---|---|---|
| Feed | 997.35 | 23.5 | 33.4 | 27.3 | 2.4 | 26.7 | 2.4 | 32.0 | 9.3 |
| Residue | 107.39 | 0.4 | 1.3 | 65.3 | 3.4 | 20.3 | nd | 11.0 | nd |
| TRF2 | 366.95 | 28.5 | 40.8 | 27.2 | 2.9 | 27.0 | 2.5 | 34.9 | 6.5 |
| TRF 4-10 | 4.85 | 63.6 | 74.5 | 12.3 | 2.5 | 28.2 | 3.5 | 40.3 | 13.2 |
| TRF7 | 76.78 | 62.9 | 65.7 | 3.5 | 0.7 | 21.0 | 3.7 | 47.4 | 23.7 |
| TRF8 | 11.42 | 48.0 | 48.7 | 1.3 | 0.2 | 15.1 | 3.5 | 47.9 | 32.0 |

Abbreviations:
VE—vitamin E;
T—tocopherol;
$T_1$—tocomonoenol;
$T_3$—tocotrienol;
(%)$^S$—% on sample;
(%)$^E$—% of total vitamin E content;
nd—not detected (below detection limit).

Examples I and II demonstrate that α-tocopherol removal and δ-tocotrienol enhancing are more effective by extracting saturated TRF3 in n-hexane ten times with small aliquots (200 mL) of n-hexane (α-tocopherol content 3.5%, δ-tocotrienol content 23.7%) as compare with that extracting with a single lot (2 L) with the same total volume of n-hexane (α-tocopherol content 8.7%, δ-tocotrienol content 18.7%).

Example III 508.23 g of TRF was extracted with 2.0 L neat methanol in a separating funnel. The bottom oily layer was separated and re-extracted with another 2.0 L neat methanol. The step was repeated and the material was extracted for a total of 10 times. The methanol-insoluble material (residue) was rotary evaporated and 145.60 g was obtained (the content contains mainly triacylglycerols and diacylglycerols). 2.0 L of distilled water was added to the pooled methanol extract TRF1 (20 L). An oily layer was separated as the bottom layer and rotary evaporated to obtain 192.60 g TRF2. The TRF3 extract was saturated with 1.1 L n-hexane and extracted with 15 aliquots of 100 mL n-hexane each. The upper layer is TRF4 in n-hexane and the solution was rotary evaporated to dryness to remove n-hexane. The bottom TRF5 layer is rotary evaporated until the clear solution turn milky. A bottom oily layer separates from the top TRF6 solution. After rotary evaporation of the oily layer, 56.44 g of TRF7 was obtained. TRF6 solution was extracted five times with 100 mL n-hexane each. After rotary evaporation for n-hexane removal, TRF8-1 to TRF8-5 are obtained. The raffinate is a solution containing monoacylglycerols. Table 3 summarises the characteristics of the fractions obtained.

Example IV 515.94 g of TRF was extracted with 2.0 L neat methanol in a separating funnel. The bottom oily layer was separated and re-extracted with another 2.0 L neat methanol. The step was repeated and the material was extracted for a total of 10 times. The methanol-insoluble material (residue) was rotary evaporated and 140.44 g was obtained (the content contains mainly triacylglycerols and diacylglycerols). 3.0 L of distilled water was added to the pooled methanol extract TRF1 (20 L). An oily layer was separated as the bottom layer and rotary evaporated to obtain 168.56 g TRF2. The TRF3 extract was saturated with 800 mL n-hexane and extracted with 15 aliquots of 100 mL n-hexane each. The upper layer is TRF4 in n-hexane and the solution was rotary evaporated to dryness to remove n-hexane. The bottom TRF5 layer is rotary evaporated until the clear solution turn milky. A bottom oily layer separates from the top TRF6 solution. After rotary evaporation of the oily layer, 30.34 g of TRF7 was obtained. TRF6 solution was extracted twice with 500 mL n-hexane each. After rotary evaporation for n-hexane removal, 6.14 g of TRF8-1 and 0.77 g of TRF8-2 were obtained. The raffinate is a solution containing monoacylglycerols. Table 4 summarises the characteristics of the fractions obtained.

TABLE 3

Characteristics of the fractions in Example III

| | Weight (g) | $T_3$ (%)$^S$ | VE (%)$^S$ | $\alpha$-T (%)$^E$ | $\alpha$-$T_1$ (%)$^E$ | $\alpha$-$T_3$ (%)$^E$ | $\beta$-$T_3$ (%)$^E$ | $\gamma$-$T_3$ (%)$^E$ | $\delta$-$T_3$ (%)$^E$ |
|---|---|---|---|---|---|---|---|---|---|
| Feed | 508.23 | 24.8 | 34.6 | 25.9 | 2.4 | 26.2 | 0.6 | 37.4 | 7.5 |
| Residue | 145.60 | 0.9 | 2.1 | 53.2 | 3.9 | 22.7 | 1.0 | 16.5 | 2.6 |
| TRF2 | 192.60 | 21.7 | 32.4 | 29.7 | 3.4 | 26.0 | 1.9 | 32.3 | 6.7 |
| TRF4-1 | 12.09 | 21.4 | 35.4 | 32.5 | 7.0 | 25.5 | 0.3 | 31.1 | 3.6 |
| TRF4-2 | 13.08 | 22.0 | 36.3 | 32.3 | 7.1 | 25.4 | 0.5 | 30.8 | 3.9 |
| TRF4-3 | 6.22 | 22.4 | 34.2 | 33.9 | 0.7 | 27.2 | 0.5 | 33.5 | 4.2 |
| TRF4-4 | 6.91 | 24.3 | 40.2 | 32.6 | 7.1 | 25.2 | 0.6 | 30.6 | 4.0 |
| TRF4-5 | 8.31 | 31.9 | 49.1 | 28.6 | 6.4 | 26.8 | 1.0 | 32.0 | 5.3 |
| TRF4-6 | 10.4 | 35.4 | 53.6 | 28.1 | 5.8 | 27.4 | 1.1 | 32.3 | 5.4 |
| TRF4-7 | 8.07 | 38.7 | 57.3 | 26.7 | 5.6 | 27.5 | 1.5 | 32.6 | 6.0 |
| TRF4-8 | 4.69 | 41.3 | 60.5 | 26.5 | 5.2 | 28.1 | 1.6 | 32.6 | 6.0 |
| TRF4-9 | 5.24 | 44.5 | 63.6 | 24.7 | 5.4 | 28.2 | 2.0 | 33.1 | 6.7 |
| TRF4-10 | 5.17 | 43.1 | 60.1 | 23.2 | 5.2 | 27.9 | 2.5 | 33.7 | 7.7 |
| TRF4-11 | 3.77 | 43.8 | 60.1 | 22.4 | 4.7 | 28.5 | 2.4 | 34.3 | 7.7 |
| TRF4-12 | 2.85 | 45.8 | 63.8 | 22.5 | 5.7 | 27.9 | 2.7 | 33.6 | 7.6 |
| TRF4-13 | 2.42 | 46.7 | 62.7 | 21.0 | 4.6 | 29.1 | 2.4 | 35.2 | 7.7 |
| TRF4-14 | 2.41 | 51.4 | 67.7 | 19.5 | 4.7 | 28.4 | 3.1 | 35.4 | 9.0 |
| TRF4-15 | 1.92 | 57.0 | 74.7 | 19.6 | 4.1 | 29.4 | 2.8 | 35.7 | 8.4 |
| TRF7 | 56.44 | 66.9 | 72.7 | 6.7 | 1.3 | 23.8 | 3.8 | 44.7 | 19.8 |
| TRF8-1 | 5.20 | 63.2 | 66.0 | 3.4 | 0.7 | 20.7 | 3.6 | 48.0 | 23.5 |
| TRF8-2 | 5.22 | 72.7 | 75.4 | 3.0 | 0.6 | 19.8 | 3.9 | 46.7 | 25.9 |
| TRF8-3 | 1.68 | 68.4 | 70.6 | 2.6 | 0.5 | 18.4 | 3.8 | 46.9 | 27.7 |
| TRF8-4 | 0.78 | 69.4 | 71.6 | 2.5 | 0.5 | 15.9 | 4.0 | 45.6 | 31.5 |
| TRF8-5 | 0.41 | 63.8 | 65.2 | 1.7 | 0.3 | 12.0 | 4.1 | 44.8 | 37.2 |

Abbreviations:

VE—vitamin E;

T—tocopherol;

$T_1$—tocomonoenol;

$T_3$—tocotrienol;

(%)$^S$—% on sample;

(%)$^E$—% of total vitamin E content.

TABLE 4

Characteristics of the fractions in Example IV

| | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| Feed | 515.94 | 24.8 | 34.6 | 25.9 | 2.4 | 26.2 | 0.6 | 37.4 | 7.5 |
| Residue | 140.44 | nd | 0.23 | 0.23 | nd | nd | nd | nd | nd |
| TRF2 | 168.56 | 19.9 | 31.7 | 32.1 | 5.3 | 26.5 | 0.2 | 32.4 | 3.5 |
| TRF4-1 | 45.45 | 32.6 | 48.1 | 27.8 | 4.3 | 26.8 | 0.7 | 34.5 | 5.8 |
| TRF4-2 | 29.61 | 33.9 | 49.2 | 26.5 | 4.7 | 26.4 | 1.2 | 34.5 | 6.8 |
| TRF4-3 | 21.92 | 36.8 | 52.8 | 25.8 | 4.5 | 26.6 | 1.3 | 35.0 | 6.9 |
| TRF4-4 | 19.63 | 38.6 | 54.3 | 24.6 | 4.3 | 26.8 | 1.5 | 35.4 | 7.5 |
| TRF4-5 | 9.59 | 46.0 | 63.1 | 23.0 | 4.1 | 27.2 | 1.9 | 35.8 | 8.1 |
| TRF4-6 | 6.37 | 48.5 | 65.2 | 21.7 | 4.0 | 27.6 | 2.1 | 36.2 | 8.5 |
| TRF4-7 | 5.71 | 51.2 | 68.1 | 20.7 | 4.0 | 27.9 | 2.5 | 36.2 | 8.7 |
| TRF4-8 | 2.11 | 50.7 | 66.0 | 19.4 | 3.8 | 28.1 | 2.7 | 36.8 | 9.3 |
| TRF4-9 | 3.74 | 57.0 | 71.5 | 17.0 | 3.4 | 28.3 | 3.2 | 37.6 | 10.6 |
| TRF4-10 | 2.68 | 63.3 | 77.2 | 15.0 | 3.0 | 28.8 | 3.3 | 38.9 | 11.0 |
| TRF4-11 | 2.47 | 63.3 | 75.5 | 13.2 | 2.9 | 28.4 | 3.9 | 39.4 | 12.3 |
| TRF4-12 | 2.22 | 64.8 | 74.5 | 10.8 | 2.2 | 28.7 | 3.2 | 42.0 | 13.1 |
| TRF4-13 | 1.40 | 70.6 | 80.2 | 9.8 | 2.1 | 28.1 | 3.7 | 42.0 | 14.3 |
| TRF4-14 | 1.21 | 73.9 | 82.5 | 8.5 | 1.9 | 28.3 | 3.8 | 43.0 | 14.5 |
| TRF4-15 | 1.49 | 74.1 | 81.5 | 7.4 | 1.7 | 28.0 | 4.0 | 43.6 | 15.3 |
| TRF7 | 30.34 | 60.0 | 60.6 | 0.8 | 0.1 | 16.8 | 4.3 | 47.6 | 30.3 |
| TRF8-1 | 6.14 | 59.3 | 59.8 | 0.8 | 0.1 | 16.6 | 4.1 | 48.1 | 30.4 |
| TRF8-2 | 0.77 | 25.3 | 25.3 | 0.3 | 0.01 | 12.0 | 2.5 | 48.8 | 36.5 |

Abbreviations:
VE—vitamin E;
T—tocopherol;
$T_1$—tocomonoenol;
$T_3$—tocotrienol;
$(\%)^S$—% on sample;
$(\%)^E$—% of total vitamin E content;
nd—not detected (below detection limit).

Example IV demonstrates that the α-tocopherol contents in TRF7 and TRF8 are 0.8% or lower and the β-, γ- and δ-tocotrienol contents are enhanced.

Example V

TRF2 of the Example IV was used as the feed material. 168.56 g of the feed was extracted with 600 mL neat methanol in a separating funnel. The bottom oily layer was separated and re-extracted with another 600 mL neat methanol. The step was repeated and the material was extracted for a total of 10 times. The methanol-insoluble material (residue) was rotary evaporated and 52.24 g was obtained (the content contains mainly triacylglycerols and diacylglycerols). 1.0 L of distilled water was added to the pooled methanol extract TRF1 (6 L). An oily layer was separated as the bottom layer and rotary evaporated to obtain 76.93 g TRF2. The TRF3 extract was saturated with 200 mL n-hexane and extracted with 5 aliquots of 100 mL n-hexane each. The upper layer is TRF4 in n-hexane and the solution was rotary evaporated to dryness to remove n-hexane. The bottom TRF5 layer is rotary evaporated until the clear solution turn milky. A bottom oily layer separates from the top TRF6 solution. The whole content was extracted twice with 500 mL n-hexane each. After rotary evaporation for n-hexane removal, 5.48 g of TRF8-1 and 0.41 g of TRF8-2 were obtained. The raffinate is a solution containing monoacylglycerols. Table 5 summarises the characteristics of the fractions obtained.

TABLE 5

Characteristics of the fractions in Example V

| | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| Feed | 168.56 | 19.9 | 31.7 | 32.1 | 5.3 | 26.5 | 0.2 | 32.4 | 3.5 |
| Residue | 52.24 | 4.3 | 9.7 | 48.3 | 8.0 | 24.1 | nd | 19.7 | nd |
| TRF2 | 76.93 | 19.5 | 33.4 | 36.4 | 5.4 | 26.7 | 0.2 | 29.5 | 1.8 |
| TRF4-1 | 19.34 | 31.4 | 47.8 | 29.2 | 5.0 | 26.9 | 1.0 | 33.5 | 4.3 |
| TRF4-2 | 4.44 | 43.3 | 61.3 | 24.7 | 4.8 | 28.0 | 1.8 | 35.1 | 5.7 |
| TRF4-3 | 2.89 | 52.6 | 68.1 | 18.7 | 4.1 | 28.4 | 3.0 | 37.6 | 8.2 |
| TRF4-4 | 1.73 | 62.0 | 74.2 | 13.5 | 2.9 | 29.1 | 3.5 | 41.3 | 9.8 |
| TRF4-5 | 1.11 | 68.7 | 77.3 | 9.0 | 2.1 | 28.2 | 4.5 | 43.7 | 12.5 |

TABLE 5-continued

Characteristics of the fractions in Example V

|  | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| TRF8-1 | 5.48 | 60.2 | 60.5 | 0.5 | 0.01 | 16.6 | 4.4 | 49.3 | 29.1 |
| TRF8-2 | 0.41 | 33.1 | 33.3 | 0.5 | 0.01 | 14.4 | 4.0 | 48.5 | 32.6 |

Abbreviations:
VE—vitamin E;
T—tocopherol;
$T_1$—tocomonoenol;
$T_3$—tocotrienol;
$(\%)^S$—% on sample;
$(\%)^E$—% of total vitamin E content;
nd—not detected (below detection limit).

Example VI

The combined fraction of TRF4-1 to TRF4-5 of the Example IV was used as the feed material. 126.20 g of the feed was dissolved in 4.0 L neat methanol in a separating funnel. 600 mL of distilled water was added to the methanol solution. An oily layer was separated as the bottom layer and rotary evaporated to obtain 75.68 g TRF2. The top layer, TRF3 was saturated with 100 mL n-hexane and extracted with 5 aliquots of 100 mL n-hexane each. The upper layer is TRF4 in n-hexane and the solution was rotary evaporated to dryness to remove n-hexane. The bottom TRF5 layer is rotary evaporated until the clear solution turn milky. A bottom oily layer separates from the top TRF6 solution. The whole content was extracted twice with 500 mL n-hexane each. After rotary evaporation for n-hexane removal, 3.15 g of TRF8-1 and 1.97 g of TRF8-2 were obtained. The raffinate is a solution containing monoacylglycerols. Table 6 summarises the characteristics of the fractions obtained.

TABLE 6

Characteristics of the fractions in Example VI

|  | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| Feed | 126.20 | 35.6 | 51.3 | 26.3 | 4.4 | 26.7 | 1.2 | 34.8 | 6.7 |
| TRF2 | 75.68 | 25.4 | 41.2 | 32.6 | 5.8 | 26.8 | 0.8 | 30.7 | 3.4 |
| TRF4-1 | 8.68 | 34.9 | 52.9 | 29.2 | 4.8 | 27.6 | 0.7 | 33.4 | 4.4 |
| TRF4-2 | 11.02 | 44.8 | 63.0 | 24.3 | 4.6 | 27.6 | 1.8 | 35.3 | 6.5 |
| TRF4-3 | 4.38 | 55.9 | 72.1 | 18.6 | 3.8 | 28.4 | 2.9 | 37.8 | 8.5 |
| TRF4-4 | 2.08 | 66.5 | 78.3 | 12.2 | 2.9 | 27.8 | 2.9 | 40.3 | 11.9 |
| TRF4-5 | 1.25 | 78.1 | 85.5 | 7.0 | 1.7 | 27.0 | 6.0 | 43.4 | 14.8 |
| TRF8-1 | 3.15 | 83.5 | 83.9 | 0.4 | 0.02 | 14.9 | 7.2 | 44.8 | 32.7 |
| TRF8-2 | 1.97 | 77.8 | 78.1 | 0.4 | 0.01 | 13.9 | 7.0 | 44.1 | 34.6 |

Abbreviations:
VE—vitamin E;
T—tocopherol;
$T_1$—tocomonoenol;
$T_3$—tocotrienol;
$(\%)^S$—% on sample;
$(\%)^E$—% of total vitamin E content.

Examples V and VI demonstrate that fractions obtained can be recycled as feed material to be fractionated into products with α-tocopherol content of 0.5% or lower and with enhanced β-, γ- and δ-tocotrienol contents.

Example VII

The yield and quality of the tocotrienol product is also affected by the number of aliquot of n-hexane used for extraction of TRF3. Table 7 summarises the results calculated from Table 4. The data shown in Table 7 are for the calculated combined fraction of TRF7, TRF8-1 and TRF8-2.

TABLE 7

The effect of number of n-hexane extraction on yield and vitamin E composition

| No. of extraction | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| 0 | 192.85 | 43.5 | 56.0 | 19.9 | 3.4 | 25.0 | 2.0 | 37.8 | 11.9 |
| 1 | 147.40 | 46.8 | 58.4 | 17.5 | 3.1 | 24.4 | 2.4 | 38.9 | 13.7 |

TABLE 7-continued

The effect of number of n-hexane extraction on yield and vitamin E composition

| No. of extraction | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| 2 | 117.79 | 50.1 | 60.8 | 15.2 | 2.7 | 23.9 | 2.7 | 40.0 | 15.5 |
| 3 | 95.87 | 53.1 | 62.6 | 12.8 | 2.3 | 23.3 | 3.0 | 41.1 | 17.4 |
| 4 | 76.24 | 56.9 | 64.7 | 9.7 | 1.8 | 22.4 | 3.4 | 42.6 | 20.0 |
| 5 | 66.65 | 58.4 | 64.9 | 7.8 | 1.5 | 21.7 | 3.7 | 43.6 | 21.7 |
| 6 | 60.28 | 59.5 | 64.9 | 6.4 | 1.2 | 21.1 | 3.8 | 44.3 | 23.1 |
| 7 | 54.57 | 60.3 | 64.6 | 4.9 | 1.0 | 20.4 | 4.0 | 45.2 | 24.6 |
| 8 | 52.46 | 60.7 | 64.5 | 4.3 | 0.8 | 20.1 | 4.0 | 45.5 | 25.2 |
| 9 | 48.72 | 61.0 | 64.0 | 3.3 | 0.6 | 19.4 | 4.1 | 46.1 | 26.3 |
| 10 | 46.04 | 60.9 | 63.2 | 2.6 | 0.5 | 18.9 | 4.1 | 46.6 | 27.2 |
| 11 | 43.57 | 60.7 | 62.5 | 2.0 | 0.4 | 18.4 | 4.1 | 47.0 | 28.1 |
| 12 | 41.35 | 60.5 | 61.9 | 1.6 | 0.3 | 17.8 | 4.2 | 47.2 | 28.9 |
| 13 | 39.95 | 60.2 | 61.2 | 1.3 | 0.2 | 17.4 | 4.2 | 47.4 | 29.4 |
| 14 | 38.74 | 59.7 | 60.6 | 1.0 | 0.2 | 17.1 | 4.2 | 47.5 | 29.9 |
| 15 | 37.25 | 59.2 | 59.7 | 0.8 | 0.1 | 16.7 | 4.2 | 47.7 | 30.4 |

No. of extraction means number of 100 mL aliquot used for extracting TRF3.
Abbreviations:
VE—vitamin E;
T—tocopherol;
$T_1$—tocomonoenol;
$T_3$—tocotrienol;
$(\%)^S$—% on sample;
$(\%)^E$—% of total vitamin E content.

Table 7 demonstrates that the composition of the tocotrienol product can be controlled by the number of extraction of TRF3 with n-hexane. For example, if 7 extractions are carried out, the α-tocopherol content is 4.9% and the product yield is 10.6%. If 15 extractions are carried out, the α-tocopherol content is 0.8% and the product yield is 7.2%. Examples IV and VII demonstrate that a wide range of tocotrienol products can be obtained by the process in the present invention, as reflected by the compositions of the tocotrienol products in TRF7, TRF8-1 and TRF8-2 or their combined fractions, and also in TRF4-1 to TRF4-15.

Example VIII 496.53 g of TRF was dissolved in 3.0 L n-hexane and pumped into a liquid-liquid extractor. 20 L of 50% aqueous methanol (v/v) was used to remove the monoacylglycerol from the tocotrienol-rich fraction solution as the extract whereas the raffinate in n-hexane was retained in the liquid-liquid extractor. 20 L of 20% aqueous methanol (v/v) was pumped into the liquid-liquid extractor containing tocotrienol-rich fraction in n-hexane. The extract in aqueous methanol was collected in five aliquots whereas the raffinate in n-hexane was again retained in the liquid-liquid extractor. The extracts were rotary evaporated until it turned milky and further extracted with 1 L n-hexane each, separated and the n-hexane was rotary evaporated to obtain M20-1 to M20-5, respectively. 20 L of 15% aqueous methanol (v/v) was pumped into the liquid-liquid extractor containing tocotrienol-rich fraction in n-hexane. The extract in aqueous methanol was collected in five aliquots. The extracts were rotary evaporated until it turned milky and further extracted with 1 L n-hexane each, separated and the n-hexane was rotary evaporated to obtain M15-1 to M15-5, respectively. The raffinate in n-hexane was collected and rotary evaporated. Table 8 summarises the characteristics of the fractions obtained.

TABLE 8

Characteristics of the fractions in Example VIII

| | Weight (g) | $T_3$ $(\%)^S$ | VE $(\%)^S$ | α-T $(\%)^E$ | α-$T_1$ $(\%)^E$ | α-$T_3$ $(\%)^E$ | β-$T_3$ $(\%)^E$ | γ-$T_3$ $(\%)^E$ | δ-$T_3$ $(\%)^E$ |
|---|---|---|---|---|---|---|---|---|---|
| Feed | 496.52 | 28.3 | 37.4 | 22.3 | 2.2 | 25.5 | 1.5 | 39.2 | 9.4 |
| M20-1 | 3.63 | 10.3 | 10.8 | 4.8 | 0.3 | 16.1 | 2.1 | 47.5 | 29.2 |
| M20-2 | 1.55 | 11.6 | 12.0 | 3.2 | 0.2 | 14.8 | 2.4 | 48.4 | 31.0 |
| M20-3 | 1.73 | 1.73 | 1.79 | 3.3 | 0.3 | 14.7 | 2.9 | 49.0 | 29.8 |
| M20-4 | 0.62 | 20.2 | 21.0 | 3.5 | 0.3 | 13.6 | 2.8 | 50.9 | 29.0 |
| M20-5 | 0.46 | 20.0 | 21.8 | 7.6 | 0.7 | 15.9 | 2.8 | 46.3 | 26.8 |
| M15-1 | 6.70 | 40.8 | 42.7 | 3.9 | 0.5 | 16.6 | 2.9 | 49.1 | 27.0 |
| M15-2 | 6.08 | 49.1 | 52.1 | 5.1 | 0.8 | 17.9 | 3.6 | 45.8 | 26.8 |
| M15-3 | 4.81 | 55.0 | 58.2 | 4.8 | 0.7 | 16.4 | 3.8 | 47.2 | 27.1 |
| M15-4 | 4.30 | 54.4 | 57.7 | 4.9 | 0.8 | 16.4 | 4.1 | 46.4 | 27.4 |

TABLE 8-continued

Characteristics of the fractions in Example VIII

| | Weight (g) | $T_3$ (%)$^S$ | VE (%)$^S$ | α-T (%)$^E$ | α-$T_1$ (%)$^E$ | α-$T_3$ (%)$^E$ | β-$T_3$ (%)$^E$ | γ-$T_3$ (%)$^E$ | δ-$T_3$ (%)$^E$ |
|---|---|---|---|---|---|---|---|---|---|
| M15-5 | 2.96 | 59.3 | 63.4 | 5.6 | 0.9 | 17.8 | 3.9 | 46.1 | 25.8 |
| Raffinate | 455.38 | 17.8 | 24.9 | 26.5 | 3.3 | 26.3 | 1.6 | 35.2 | 8.1 |

Abbreviations:
VE—vitamin E;
T—tocopherol;
$T_1$—tocomonoenol;
$T_3$—tocotrienol;
(%)$^S$—% on sample;
(%)$^E$—% of total vitamin E content.

Example IX 504.71 g of TRF was extracted with 2.0 L neat methanol in a separating funnel. The bottom oily layer was separated and re-extracted with another 2.0 L neat methanol. The step was repeated and the material was extracted for a total of 10 times. The methanol-insoluble material (residue) was rotary evaporated and 208.30 g of the residue was obtained (the content contains mainly triacylglycerols and diacylglycerols). 20 L of distilled water was added to the pooled methanol extract TRF1 (20 L). The 40 L emulsion was pumped into a liquid-liquid extractor pre-filled with 3.0 L n-hexane. The extract in aqueous methanol was collected (contains monoacylglycerols) whereas the raffinate in n-hexane was retained in the liquid-liquid extractor. 20 L of 20% aqueous methanol (v/v) was pumped into the liquid-liquid extractor containing the raffinate in n-hexane. The extract in aqueous methanol was collected whereas the raffinate in n-hexane was again retained in the liquid-liquid extractor. The extracts in methanol were rotary evaporated until it turned milky and further extracted three times with 1 L n-hexane each, separated and the n-hexane was rotary evaporated to obtain M20-1 to M20-3. 20 L of 15% aqueous methanol (v/v) was pumped into the liquid-liquid extractor containing the raffinate in n-hexane. The extract in aqueous methanol was collected. The extracts were rotary evaporated until it turned milky and further extracted twice with 1 L n-hexane each, separated and the n-hexane was rotary evaporated to obtain M15-1 and M15-2. The raffinate in n-hexane was collected and rotary evaporated. Table 9 summarises the characteristics of the fractions obtained.

TABLE 9

Characteristics of the fractions in Example IX

| | Weight (g) | $T_3$ (%)$^S$ | VE (%)$^S$ | α-T (%)$^E$ | α-$T_1$ (%)$^E$ | α-$T_3$ (%)$^E$ | β-$T_3$ (%)$^E$ | γ-$T_3$ (%)$^E$ | δ-$T_3$ (%)$^E$ |
|---|---|---|---|---|---|---|---|---|---|
| Feed | 504.71 | 28.3 | 37.4 | 22.3 | 2.2 | 25.5 | 1.5 | 39.2 | 9.4 |
| Residue | 208.30 | 5.0 | 8.6 | 39.6 | 2.2 | 26.0 | nd | 31.0 | 1.3 |
| M20-1 | 20.11 | 29.5 | 30.6 | 3.5 | 0.1 | 14.0 | 2.8 | 49.1 | 30.5 |
| M20-2 | 2.50 | 23.5 | 24.6 | 4.6 | 0.01 | 14.8 | 2.0 | 49.0 | 2.96 |
| M20-3 | 0.37 | 3.9 | 4.0 | 2.6 | 0.01 | 12.1 | 1.1 | 59.7 | 24.6 |
| M15-1 | 23.46 | 62.1 | 66.7 | 6.0 | 1.0 | 18.8 | 5.3 | 42.8 | 26.2 |
| M15-2 | 0.61 | 53.2 | 56.8 | 5.6 | 0.6 | 15.9 | 4.7 | 41.9 | 31.3 |
| Raffinate | 207.20 | 32.0 | 46.4 | 27.3 | 3.7 | 27.6 | 0.8 | 34.6 | 6.0 |

Abbreviations:
VE—vitamin E;
T—tocopherol;
$T_1$—tocomonoenol;
$T_3$—tocotrienol;
(%)$^S$—% on sample;
(%)$^E$—% of total vitamin E content;
nd—not detected (below detection limit).

Example X 501.15 g of TRF was extracted with 2.0 L neat methanol in a separating funnel. The bottom oily layer was separated and re-extracted with another 2.0 L neat methanol. The step was repeated and the material was extracted for a total of 10 times. The methanol-insoluble material (residue) was rotary evaporated and 134.17 g of the residue was obtained (the content contains mainly triacylglycerols and diacylglycerols). 20 L of distilled water was added to the pooled methanol extract TRF1 (20 L). The 40 L emulsion was extracted with 4.0 L n-hexane. The bottom aqueous methanol layer was (contains monoacylglycerols) separated from the top n-hexane layer. 20 L of 25% aqueous methanol (v/v) was added to the n-hexane layer, mixed well and separated. The extracts in methanol were rotary evaporated until it turned milky and further extracted twice with 1 L n-hexane each, separated and the n-hexane was rotary evaporated to obtain M25-1 and M25-2, respectively. The n-hexane layer after extracted with 25% aqueous methanol was further extracted with 20 L of 20% aqueous methanol (v/v). The extracts in methanol were rotary evaporated until it turned milky and further extracted twice with 1 L n-hexane each, separated and the n-hexane was rotary evaporated to obtain M20-1 and M20-2, respectively. The n-hexane layer after extracted with 25% aqueous methanol was further extracted with 20 L of 15% aqueous methanol (v/v). The extracts in methanol were rotary evaporated until it turned milky and further extracted twice with 1 L n-hexane each, separated and the n-hexane was rotary evaporated to obtain M15-1 and M15-2, respectively. The raffinate in n-hexane was collected and rotary evaporated. Table 10 summarises the characteristics of the fractions obtained.

TABLE 10

Characteristics of the fractions in Example X

|  | Weight (g) | $T_3$ (%)$^S$ | VE (%)$^S$ | α-T (%)$^E$ | α-$T_1$ (%)$^E$ | α-$T_3$ (%)$^E$ | β-$T_3$ (%)$^E$ | γ-$T_3$ (%)$^E$ | δ-$T_3$ (%)$^E$ |
|---|---|---|---|---|---|---|---|---|---|
| Feed | 501.15 | 28.3 | 37.4 | 22.3 | 2.2 | 25.5 | 1.5 | 39.2 | 9.4 |
| Residue | 134.17 | 0.9 | 2.5 | 62.2 | 2.0 | 23.2 | nd | 12.7 | nd |
| M25-1 | 12.41 | 20.2 | 21.2 | 4.4 | 0.2 | 17.9 | 1.1 | 50.3 | 26.2 |
| M25-2 | 0.72 | 18.7 | 20.8 | 9.4 | 0.6 | 20.0 | 1.3 | 46.9 | 21.8 |
| M20-1 | 13.47 | 42.6 | 45.2 | 5.3 | 0.5 | 18.5 | 2.8 | 47.5 | 25.4 |
| M20-2 | 1.80 | 40.4 | 42.9 | 5.2 | 0.5 | 18.0 | 2.9 | 47.7 | 25.8 |
| M15-1 | 24.56 | 64.8 | 70.4 | 7.1 | 0.9 | 19.9 | 3.5 | 46.3 | 22.5 |
| M15-2 | 1.22 | 41.3 | 45.1 | 7.5 | 0.8 | 19.9 | 2.8 | 47.7 | 21.4 |
| Raffinate | 297.40 | 26.8 | 36.6 | 24.5 | 2.5 | 26.8 | 1.7 | 37.0 | 7.7 |

Abbreviations:
VE—vitamin E;
T—tocopherol;
$T_1$—tocomonoenol;
$T_3$—tocotrienol;
(%)$^S$—% on sample;
(%)$^E$—% of total vitamin E content;
nd—not detected (below detection limit).

It should be noted that configurations of the various components, elements, systems and/or methods used in carrying out the above-mentioned embodiments are illustrative and exemplary only. One of ordinary skill in the art would recognize that those configurations, components, elements, systems and/or methods used herein may be altered in a manner so as to obtain different effects or desired operating characteristics. As such, the approach as described above should not be construed as limiting, but as the best mode contemplated by the inventor for carrying out the invention. Such variations are not to be regarded as a departure from the principle and scope of the invention, and all such modifications as would be obvious to one skilled in the art are intended to be included within the scope of following claims.

The invention claimed is:

1. A process for modifying the composition of Vitamin E in tocotrienol-rich fraction (TRF) characterized by reducing or removing α-tocopherol content from a TRF feed material and/or enhancing the content of β- and δ-tocotrienol in Vitamin E concentrate by a process of solvent extraction and fractionation of TRF feed material, wherein the process of solvent extraction and fractionation for reducing or removing α-tocopherol and enhancing the content of β-and δ-tocotrienol in vitamin E concentrate comprises subjecting the TRF feed material to a process comprising the steps of:
 a. dissolving the TRF feed material in an alcohol to produce a first tocotrienol-rich fraction (TRF1) solution;
 b. removing alcohol-insoluble components from the TRF1 solution;
 c. adding water to the TRF1 solution to separate a tocotrienol-rich fraction 2 (TRF2) from a saturated tocotrienol-rich fraction 3 (TRF3) solution;
 d. saturating the TRF3 solution in aqueous alcohol with a hydrocarbon solvent to produce a TRF3a solution;
 e. extracting the TRF3a solution with addition of an additional aliquot of hydrocarbon solvent to obtain a tocotrienol-rich fraction 4 (TRF4) solution in hydrocarbon solvent and a tocotrienol-rich fraction 5 (TRF5) solution;
 f. separating the TRF4 solution from the TRF5 solution obtained in step (e);
 g. obtaining TRF4 by way of distillation of the TRF4 solution obtained in step (f);
 h. partially removing aqueous alcohol from the TRF5 solution obtained in step (f) above by further distillation to obtain a saturated tocotrienol-rich fraction 6 (TRF6) solution and tocotrienol-rich fraction 7 (TRF7);
 i. adding hydrocarbon solvent to the saturated TRF6 solution obtained in step (h) above to obtain a tocotrienol-rich fraction 8 (TRF8) and highly polar monoacylglycerol raffinate; and
 j. removing solvent residue in TRF7 and TRF8 by distillation.

2. The process of claim 1, wherein the TRF feed material is derived from palm oil or palm fatty acid distillates or rice bran oil.

3. The process of claim 1, wherein the TRF is derived from materials other than palm oil or palm fatty acid distillates or rice bran oil.

4. The process of claim 1, wherein the alcohol used is methanol or ethanol or a mixture of methanol and ethanol or aqueous 1-propanol or 2-propanol.

5. The process of claim 1, wherein the amount of water added has an alcohol to water ratio of at least 10:1 v/v or at least 15:1 v/v.

6. The process of claim 1, wherein the hydrocarbon solvent used is n-hexane, hexanes or n-heptane or a mixture of two or more of these hydrocarbon solvents.

7. The process of claim 1, wherein the TRF3 solution is extracted with multiple aliquots of hydrocarbon solvent.

8. The process of claim 1, wherein TRF2 can be recycled as a feed material (tocotrienol-rich fraction).

9. The process of claim 1, wherein the TRF4 solution or portions of the TRF4 solution can be recycled as a feed material (tocotrienol-rich fraction).

10. The process of claim 1, wherein the TRF4 solution is a tocotrienol product with an enriched total tocotrienol content and/or with a wide range of tocotrienol product composition and can be recycled as a feed material (tocotrienol-rich fraction).

11. The process of claim 1, wherein the TRF7 and/or TRF8 provide tocotrienol products with an enriched total tocotrienol content, with reduced α-tocopherol content and/or enhanced β- and δ-tocotrienols content compared to TRF.

12. The process of claim 11, wherein the tocotrienol products have a δ-tocotrienol content exceeding 29% of the total vitamin E content by weight, or exceeding 35% of the total vitamin E content by weight, or exceeding 45% of the total vitamin E content by weight.

13. The process of claim 11, wherein the tocotrienol products have an α-tocopherol content of less than 7% of the total vitamin E content by weight, or less than 5% of the total vitamin E content by weight, or less than 1% of the total vitamin E content by weight, or less than 0.5% of the total vitamin E content by weight.

14. The process of claim 13, wherein the tocotrienol products have clinical applications.

15. The process of claim 1, wherein monoacylglycerols, triacylglycerols and diacylglycerols are removed from the TRF.

16. The process of claim 15, wherein aqueous alcohol is used to remove the monoacylglycerols after the removal of the alcohol-insoluble components.

17. The process of claim 15, wherein monoacylglycerols, triacylglycerols and diacylglycerols are removed from the TRF with a two-step methanol extraction process.

18. The process of claim 1, wherein the process is carried out without the removal of alcohol-insoluble components.

19. The process of claim 1, wherein the process is carried out at room temperature and under atmospheric pressure.

20. The process of claim 1, wherein water is used to enhance the fractionation of α-tocopherol into the n-hexane phase and the β- and δ-tocotrienols into the methanol phase.

21. The process of claim 1, wherein TRF7 and TRF8 or their combined fractions are the main tocotrienol product having low α-tocopherol content, high β- and δ-tocotrienol content and high total tocotrienol content.

22. The process of claim 1, wherein distillation of aqueous methanol and n-hexane is carried out by using a rotary evaporator or a falling film evaporator or a thin film evaporator or using any suitable distillation vessels under reduced pressure.

23. The process of claim 22, wherein the reduced pressure is between 30,000-90,000 Pa.

24. The process of claim 1, wherein monoacylglycerols are removed with aqueous methanol after or without the removal of methanol-insoluble materials.

25. The process of claim 1, wherein the TRF5 solution is distilled under partial vacuum until the clear solution turns milky to form the TRF6 solution emulsion as the top layer and TRF7 as the bottom layer.

* * * * *